(12) United States Patent
Adriani et al.

(10) Patent No.: US 11,226,326 B2
(45) Date of Patent: Jan. 18, 2022

(54) FLUID SENSOR/PLANT MACHINERY MONITORING SYSTEM INTERFACE COMPLEX AND METHOD

(71) Applicant: Spectro Scientific, Inc., Chelmsford, MA (US)

(72) Inventors: Giuseppe Adriani, Florence (IT); Matteo Paoli, Florence (IT)

(73) Assignee: Spectro Scientifics, Inc., Chelmsford, MA (US)

( * ) Notice: Subject to any disclaimer, the term of this patent is extended or adjusted under 35 U.S.C. 154(b) by 681 days.

(21) Appl. No.: 16/010,653

(22) Filed: Jun. 18, 2018

(65) Prior Publication Data
US 2018/0364212 A1    Dec. 20, 2018

Related U.S. Application Data

(60) Provisional application No. 62/522,272, filed on Jun. 20, 2017.

(51) Int. Cl.
*G01N 33/28* (2006.01)

(52) U.S. Cl.
CPC .................... *G01N 33/28* (2013.01)

(58) Field of Classification Search
CPC ..................................... G01N 33/28
USPC ........................................... 702/50
See application file for complete search history.

(56) References Cited

U.S. PATENT DOCUMENTS

| 8,958,900 B2* | 2/2015 | Steele | G05B 19/04 |
| | | | 700/108 |
| 10,895,254 B2* | 1/2021 | Beisel | G01B 7/003 |
| 2005/0180868 A1* | 8/2005 | Miller | F04B 51/00 |
| | | | 417/437 |

* cited by examiner

*Primary Examiner* — Aditya S Bhat
(74) *Attorney, Agent, or Firm* — Iandiorio Teska & Coleman, LLP

(57) ABSTRACT

A fluid sensor/plant machinery monitoring system and method wherein a plurality of on-line fluid property sensors output on-line sensor data and are connected to an interface configured with a server outputting the on-line sensor data via a network. A remote information management system requests and receives the on-line sensor data via the network, stores machine fluid property laboratory data, and calculates an estimate of one or more fluid properties based on both the received on-line sensor data and the stored laboratory data. A manifold unit receives fluid from a machine and includes ports for the on-line fluid property sensors. The remote information management system calculates one or more fluid properties based on both the received on-line sensor data and the stored laboratory data based on models where a machine fluid property is a function of both the on-line sensor data and the stored laboratory data for the machine.

10 Claims, 8 Drawing Sheets

| Sensor Data | | | 140 |
|---|---|---|---|
| Time | VISC | Particle | Quality |
| 12/14/15 8:00am | 52 | 16/12/12 | 62 |
| 12/14/15 8:05am | 56 | 16/13/13 | 62 |
| ⋮ | | | |
| 2/16/16 2:33pm | 51 | 18/17/15 | 62 |

| Lab Data | | | | | 142 |
|---|---|---|---|---|---|
| Time | VISC | Particle | TAN | $H_2O$ | Metals |
| 12/15 | 46.01 | 22/15/12 | 0.25 | 8.6 | 25 |
| 1/16 | 45.87 | 22/17/14 | 0.26 | 121 | 32 |
| 2/16 | 43.26 | 23/17/14 | 0.31 | 132 | 36 |

*FIG. 8*

FLUID SENSOR/PLANT MACHINERY MONITORING SYSTEM INTERFACE COMPLEX AND METHOD

RELATED APPLICATIONS

This application claims benefit of and priority to U.S. Provisional Application Ser. No. 62/522,272 filed Jun. 20, 2017, under 35 U.S.C. §§ 119, 120, 363, 365, and 37 C.F.R. § 1.55 and § 1.78, which is incorporated herein by this reference.

FIELD OF THE INVENTION

This invention relates to primarily to machine fluid analysis.

BACKGROUND OF THE INVENTION

In a typical industrial plant, there are machines (also called assets) such as pumps, engines, turbines, and the like which include fluid such as oil, hydraulic fluid, and the like. Various vendors provide fluid sensors such as viscometers, oil analysis spectrometers, particle counters and classifiers, and the like which can be coupled on-line with the fluid in each machine. These sensors thus output sensor data.

A typical industrial plant also employs a machinery control system and a machinery monitoring system. See, for example, U.S. Pat. Nos. 8,958,900 and 8,509,935 incorporated herein by this reference. The machinery monitoring system displays, typically in a control room for example, various machine parameters such as vibration, temperature, pressure, and the like.

In order to enable the machinery monitoring system to display the sensor data from the fluid sensors, the data analysis module of each sensor must usually be coupled to the machinery monitoring system via a specially configured interface.

For example, as between two different viscometers from two different vendors, the interface between each viscometer and a given machinery monitoring system will be different. As another example, the interface will be different as between a given viscometer and one vendor's machinery monitoring system and another different vendor's machinery monitoring system. The result may be a high cost to interface a given machinery monitoring system with on-line fluid sensors.

Moreover, the machine fluid is periodically sent to a laboratory for analysis using more sophisticated analyzers and equipment. The resulting lab report must be read by a skilled employee who then reconciles any differences between the lab data and the sensor data. In some cases, the lab data is more trustworthy. In other cases, the sensor data is more trustworthy because, for example, sensor data is more recent and/or the possibility of the lab mishandling the fluid sample.

SUMMARY OF THE INVENTION

Featured is a simpler, less expensive and easier to use system which displays and reconciles both on-line sensor data and lab data and which makes recommendations based on the same. Further, the system enables a better interface between the on-line fluid sensors and the various users of the system.

Featured is a fluid sensor/plant machinery monitoring system interface complex comprising a plurality of on-line fluid property sensors outputting on-line sensor data and connected to an interface configured with a server outputting the on-line sensor data via a network such as the internet. A remote information management system is configured to request and receive the on-line sensor data via the network, store machine fluid property laboratory data, and calculate an estimate of one or more fluid properties based on both the received on-line sensor data and the stored laboratory data.

Preferably, the system further includes a manifold unit receiving fluid from a machine and including ports for the on-line fluid property sensors. The remote information management system preferably calculates one or more fluid properties based on both the received on-line sensor data and the stored laboratory data based on models where a machine fluid property is a function of both the on-line sensor data and the stored laboratory data for the machine. The interface preferably includes an instrument server and an information server. The instrument server may include one or more sensor drivers configured to store the on-line sensor data in a memory. The information server may include one or more web servers configured to retrieve the on-line sensor data from the memory and serving the on-line sensor data via the network to the remote information management system.

Also featured is a fluid sensor/plant machinery monitoring system comprising an interface connected to one or more on-line fluid property sensors outputting on-line sensor data and including an instrument server configured to store the on-line sensor data in a memory and an information server including at least one web server configured to retrieve the on-line sensor data from the memory and to serve the on-line sensor data to a network. A remote information management system is configured to request and receive the on-line sensor data via the network, store machine fluid property laboratory data, and calculate one or more machine fluid properties based on models in which a machine fluid property is a function of the on-line sensor data and the stored fluid property laboratory data.

One fluid monitoring method comprises coupling at least one on-line fluid property sensor to a machine to provide sensor data, providing the sensor data to a common interface, serving the sensor data from the common interface to a remote information management system via a network, providing machine fluid property laboratory data to the information management system, and executing one or more models stored in the information management system to calculate an estimate of one or more machine fluid properties as a function of both the machine fluid property laboratory data and the sensor data.

Also featured is a fluid sensor/plant machinery monitoring method comprising connecting an interface to one or more on-line fluid property sensors outputting on-line sensor data, storing the on-line sensor data in a memory, serving the on-line sensor system data, to a remote management system via a network, storing machine fluid property laboratory data, and calculating one or more machine fluid properties based on models in which a machine fluid property is a function of the on-line sensor data and the stored fluid property laboratory data.

The method may further include coupling the one or more on-line fluid property sensors to a manifold unit receiving fluid from a machine.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 8 is a view of the sensor data and laboratory data output by the interface subsystem in one example.

DETAILED DESCRIPTION OF THE INVENTION

Figure 1:
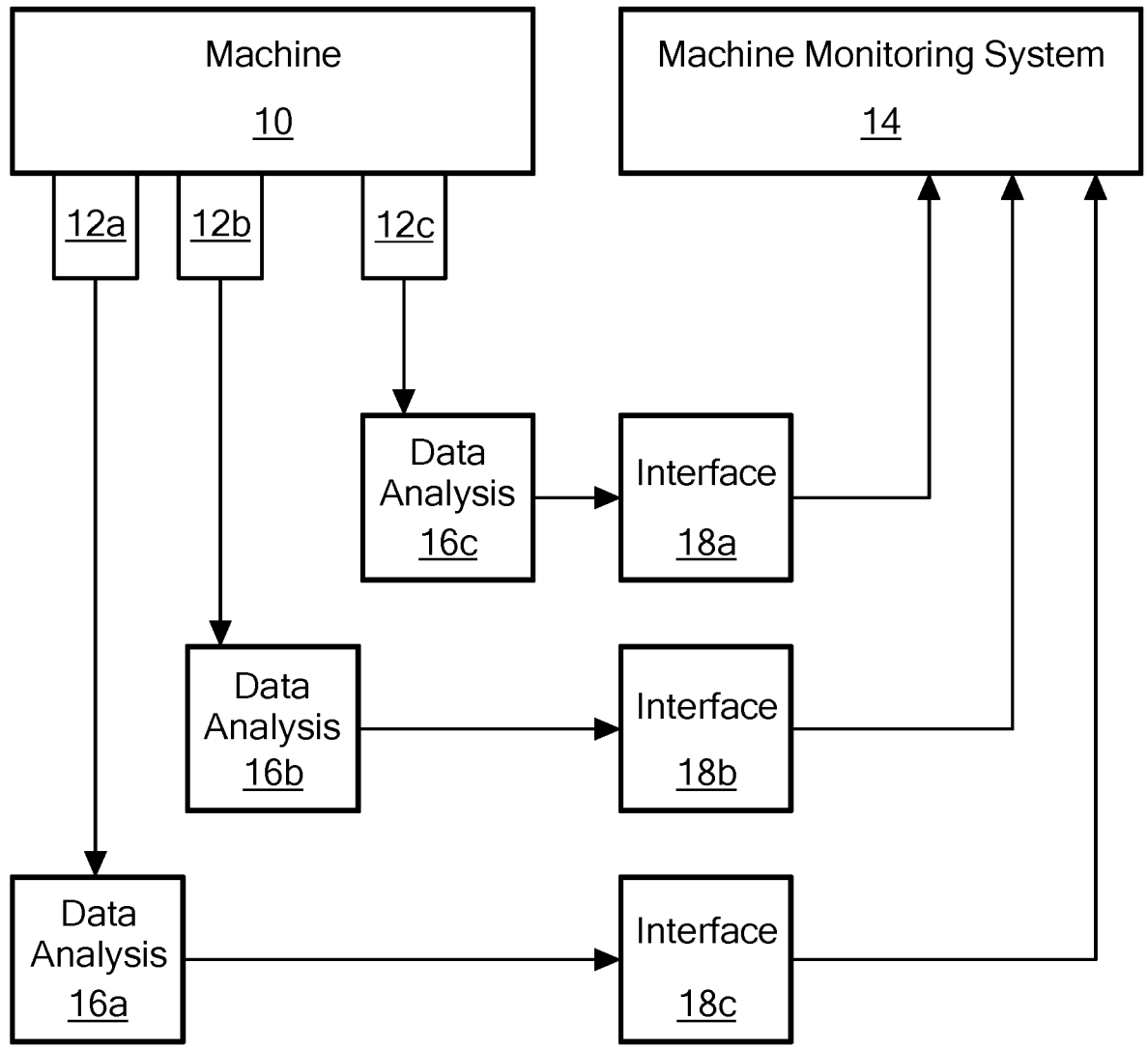
FIG. 1 is a block diagram showing the primary components associated with a method according to the prior art of interfacing a machine's on-line sensors with the plant's machinery monitoring system.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows how, in the prior art, the various on-line sensors 12a, 12b, and 12c are coupled to a machine 10 and interfaced with machinery monitoring system 14. The on-line fluid analysis sensors 12 may include viscometers, oil analysis spectrometers, particle counters, particle classifiers, and the like. Each sensor typically includes its own data analysis module 16 as shown. A specially configured interface 18 is typically required between each data module and machinery monitoring system 14. As discussed in the Background section above, the result can often be a high cost to interface a given machinery monitoring system 14 with the on-line fluid sensors 12.

Figure 2:
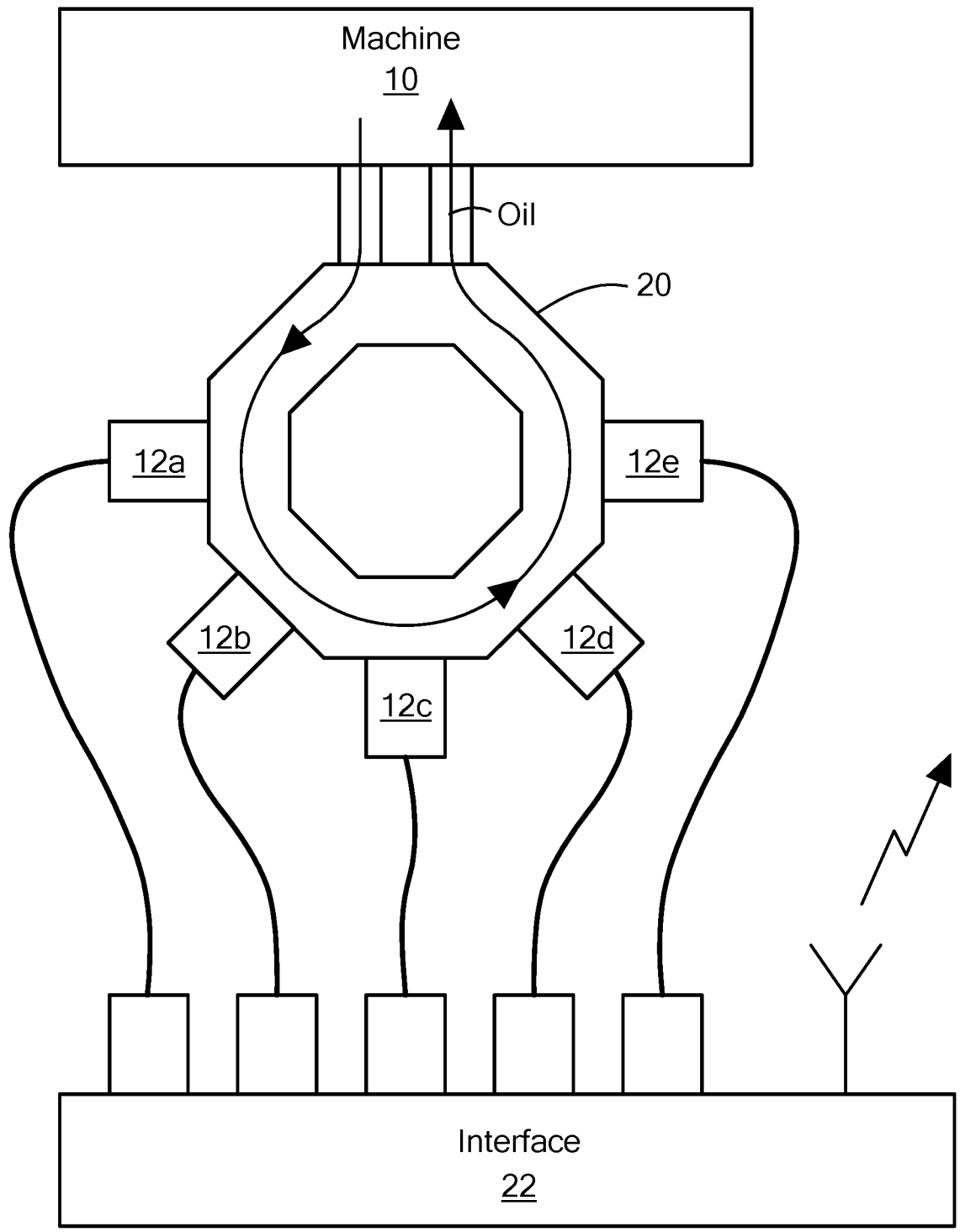
FIG. 2 is a block diagram showing an example of an interface to the on-line machine fluid sensors here coupled to a manifold.

As shown in FIG. 2, one preferred machinery monitoring system in accordance with aspects of the invention includes manifold 20 and electronic interface 22.

Manifold unit 20 receives fluid (e.g., oil) from machine 10 as shown. Oil flows around an interior flow path 24 of the manifold and sensors 12a-12e, fitted into ports of the manifold as shown, include active elements inserted into the oil and/or configurations to irradiate the oil or the like. The raw data output by each sensor 12 is fed, as shown, typically by conductors, to interface 22. The sensors may include a spectrometer, a particle shape classifier, a particle counter, a viscometer, a fluid temperature sensor, and other known sensors.

Interface 22 processes the sensor data and uploads the sensor data via the internet to a remote information management system (IMS) operating on a server. In this way, the sensor data is available via the internet to different systems and users (e.g., clients). In one embodiment, the information management system includes a modified Spectrotrack™ program suite (Spectro Scientific, Inc., Chelmsford, Mass.). Other browser based information management systems may be used if configured as disclosed herein.

Figure 3:
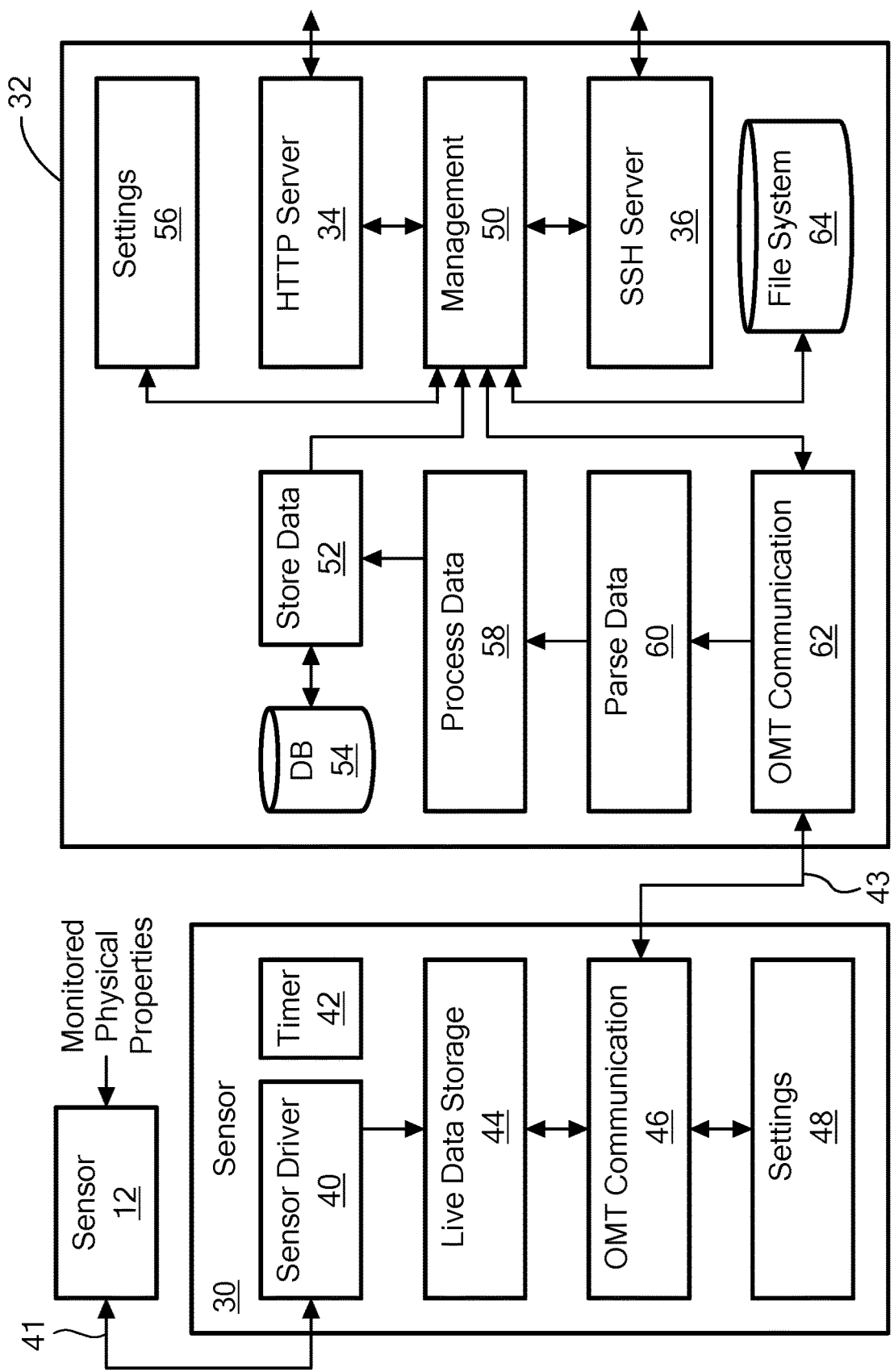
FIG. 3 is a block diagram showing the primary subsystems associated with the interface of FIG. 2.

Interface 22, FIG. 2 preferably includes, as shown in FIG. 3, instrument server 30 and information server 32. Instrument server 30 may include a microprocessor programmed to carry out the functions described herein as well as various memories. Information server 32 (which can be thought of as an Online Machine Tutor (OMT)) may be a central processing unit based subsystem programmed and configured to carry out the functions described herein. Again, one or more memories and/or databases may be included. Servers 30 and 32 may communicate using an RS45 protocol. Information server 32 preferably includes one or more web servers such as HTTP server 34 and SSH server 36 serving sensor data via the internet upon requests from a client. The client may be a remote information management system 70, FIG. 4, a user 72 (e.g., using a smart phone, tablet, or computer), and/or a local machinery monitoring system 74.

In FIG. 3, lines with single arrows depict mondirectional method calls, lines with double arrows depict bidirectional method calls (a class that can spawn more classes), and lines 41 and 43 depict physical interfaces.

Sensor Driver 40 takes as input raw sensor data (e.g., canbus Modbus i/o digital etc.) message requests from communication interface 46 and populates the data array in storage 44. This populated data may include, for example, the raw value of the viscosity in Centistokes at the ambient fluid temperature obtained from a viscosity sensor or particle counts in raw counts from a particle sensor. Sensor driver 40 connects to the sensor(s), obtains results, and provides these results as requested. Timer 42 acts as an internal time-based counter, and provides a precision clock for the system.

Live Data Storage 44 takes as input, data from driver 40 or a DBMS query from communication interface 46 and generates DBMS query results. The storage 44 stores the most recent data retrieved from the sensors. Communication Interface 46 takes as input DBMS query results from storage 44 or settings from memory 48 (to be included in message request to sensor driver 40, e.g. serial # or baud rate, etc.) and/or high-level queries (e.g., text message or even entire firmware update) from OMT communication interface 62. Interface 46 outputs DBMS query command to storage 44 (e.g., erase data), relays any changes in settings to memory 48 from OMT communication 62, and/or returns text messages back to OMT communication 62 with requested information. Interface 46 thus coordinates communication between the instrument server 30 and the information server 32.

Settings memory 48 receives and stores existing configurations (low level settings e.g. baud rates, s/n etc., register # of modus, serial port number) for sensor driver 40 and sensor 12 from OMT communications block 46.

Management block 50 receives abnormal messages from OMT 62, for (e.g., a timeout error), data from storage 52 resulting from requests, current system settings from memory 56 (e.g., how often to query for new sensor data), message requests from server 34 and server 36, and/or relevant files from file system 64, (e.g., in order to populate settings 56 and/or retrieve the web page JavaScript information for server 34).

Management block 50 instructs OMT 62 regarding what text message to send, outputs requests for data from memory 52 (e.g., last 2 months of data), updates settings 56 with fresh settings, (e.g., how often to query for new sensor data) fulfills requests from servers 34,36 and/or provides relevant files to file system 64, (e.g., new web page files). Management block 50 thus provides the core supervisory role for the entire system and orchestrates all data flow.

Storage 52 receives requests from management block 50, data from database 54, (requested stored data), and/or data from process data block 58 (the data hot off the machine). Data storage 52 outputs data to database 54 to be stored and data to management block 50 as requested. Data storage block 52 thus provides interface between the data management functions and the database itself. Database 54 stores historical data from the sensors, as well as system logs.

Settings memory block 56 receives settings from management block 50. (e.g., port number for http server, email address to send alarm when sensor value is out of range (need to advise customer and the like)). Memory 56 outputs the latest settings to management block 50. Memory 56 thus stores and provides the settings for the information server.

Process data block 58 receives as input parsed pure data from parse data block 60 (e.g., actual sensor reading level) and outputs processed data to memory 52 (e.g., turns V (any temp) to V (40 Celsius)). Block 58 changes the raw value from the sensor to customer data format, units, and syntax. For the particle count sensor, it may utilize a stored ISO code table to determine the ISO code sequence from the raw counts in Storage 44.

Parse data block 60 receives as input message from OMT 62 and checks the correct syntax (not checksum). Block 60 unpacks the message received and checks that it follows the right syntax and selects the value provided by the sensor and sends to process data.

OMT communication block 62 receives requests from management block 50 and messages from 46. Block 62 outputs information back to management 50 regarding macro errors such as timeouts, fail CRC etc. i.e. abnormal messages and sends messages along parse data if good message. Thus, OMT communication block 62 provides a low-level communication link between information server 32 and instrument server 36.

File system 64 receives new static files from management block 50 and/or requests for existing files from management block 50 and outputs requested files to management block 50. File system 64 thus provides data storage on an sd card or other storage mediums.

Upon powering the interface, (the interface typically includes a power supply circuit for powering each of the sensors), Wi-Fi and Ethernet controlled by the information server begin looking for configured networks. Preferably the Ethernet has precedence. The winning network connection obtains an IP address from a server such as a router or the like local to the plant where the machine is located. Once obtained, the system connects to a vender-established VPN server. Preferably, each information server maintains its unique authentication key. An encrypted tunnel between the information server and the VPN server is then established.

The VPN server validates the information server and assigns to it a new internal VPN IP address. In this way, each and every information server operating globally has a static IP address from the VPN server enabling it to be logged into using, for example, the instrument server number dot followed by the company name followed by .com. As an example, S23864.sprectrosci.com is for a particular information server since the DNS server maps the URL name. This vender based VPN tunnel thus goes through the customer's network. The URL name may be chosen by the customer to reflect the company name, serial number, and name of the machine being monitored, and the like.

The result is two operational IP addresses. This allows the vendor to always have access to the device for troubleshooting since it always remains in the vender network.

The vender may password-protect the URL or not. Not password protected URLs may have several advantages such as the ability to update software and firmly remotely to the interface. Also, various personnel in the company may be able to access the interface to check in on a particular asset or machine. In other embodiments, the information servers are replicable and can be set up via a supplied router instead of using the customer's network. Thus, connection between the information server and the cloud is achieved.

Figure 4:
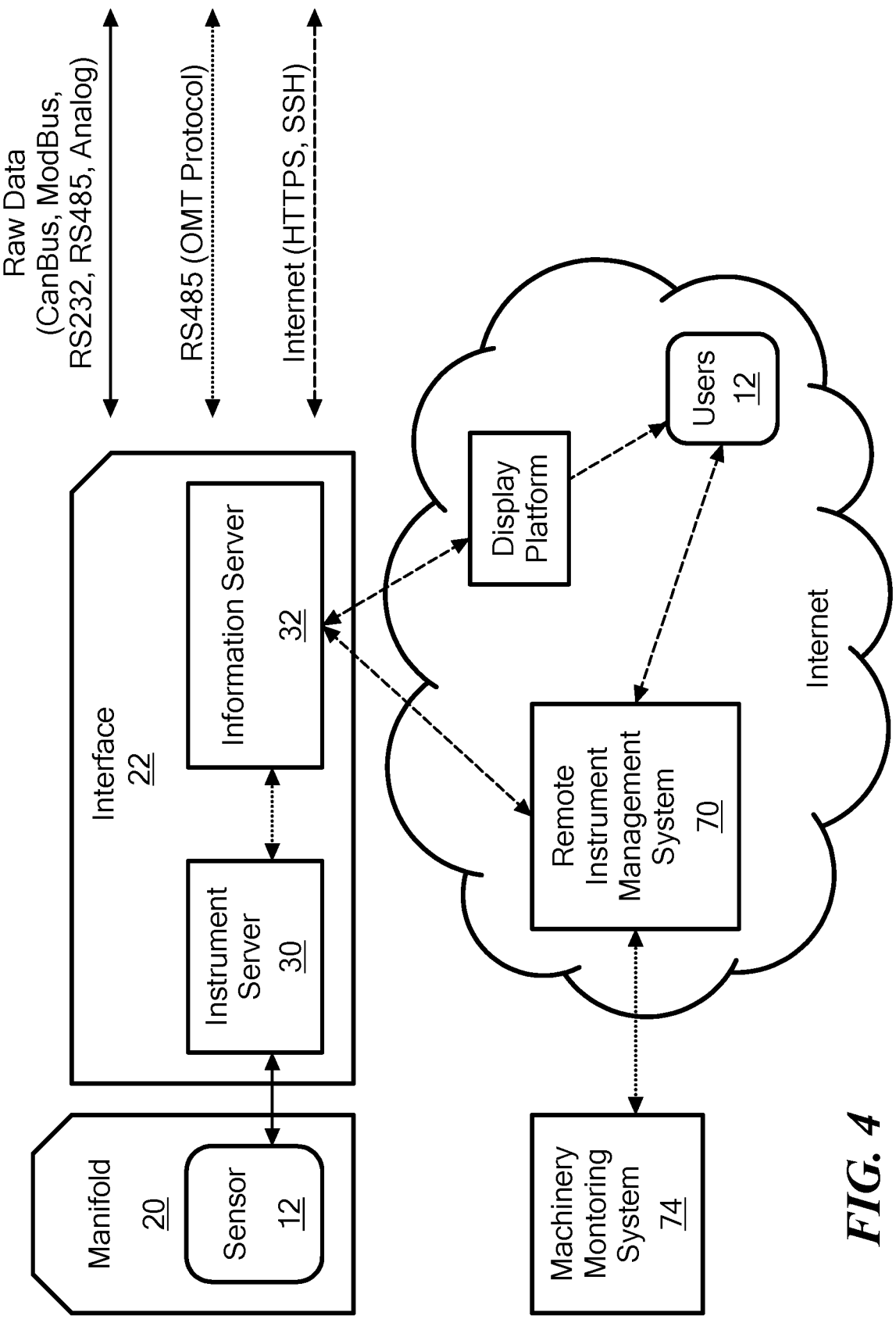
FIG. 4 is a block diagram showing the communication channels between the interface and a remote information management system (IMS) and other possible users of the sensor data.
Figure 5:
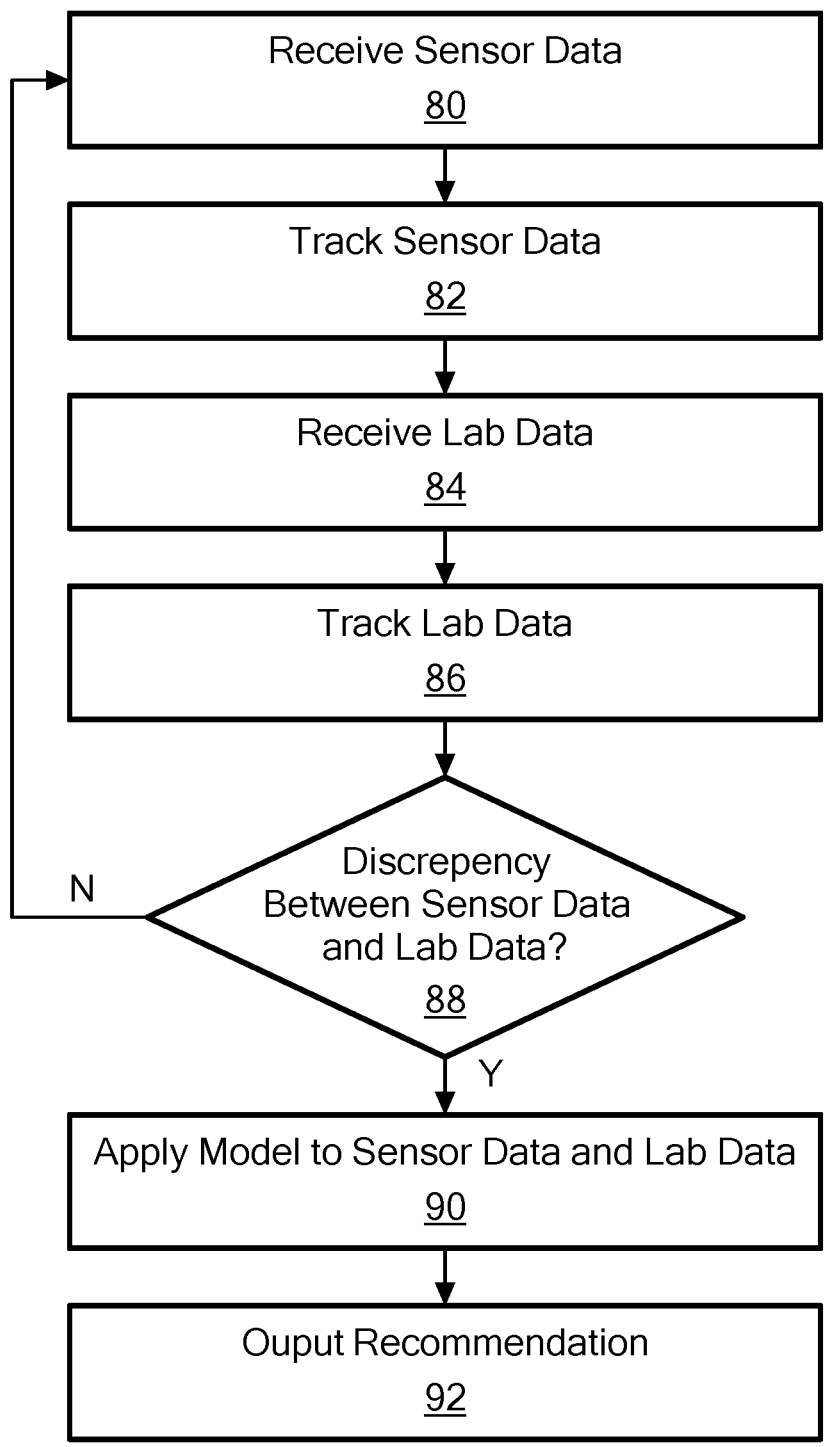
FIG. 5 is flowchart depicting, in one example, the primary steps associated with the programming of the remote information management system of FIG. 4 in order to reconcile discrepancies between sensor data and laboratory data.

Remote information management system 70, FIG. 4 is then configured, (e.g., programmed) to request and receive sensor data, step 80, FIG. 5 from the information server 32, FIGS. 3-4. The information management system typically tracks the sensor data, step 82 and also receives laboratory data, step 84 and tracks the laboratory data step 86. As shown as step 88, when there is a discrepancy (e.g., above some predetermined percentage) between the sensor data and the lab data, a mathematical model may be applied automatically by the information management system 70 to the sensor data and lab data in order to output one or more recommendations, step 92.

Figure 6:
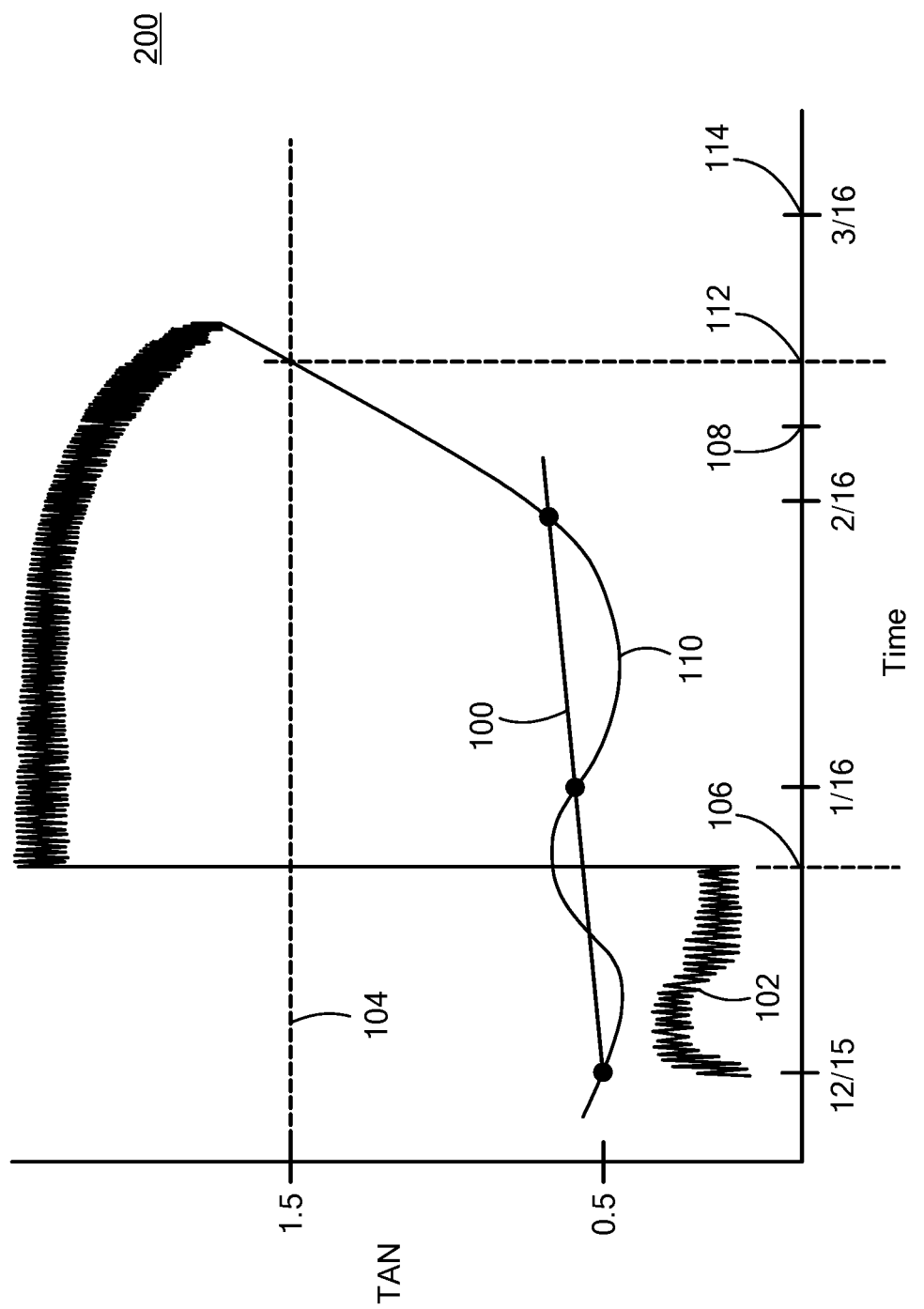
FIG. 6 is an exemplary graph showing plotted sensor data, plotted laboratory data, and a plotted mathematical model calculation used to estimate when a machine fluid parameter will exceed a set limit.

In one example, as shown in FIG. 6, the laboratory data 100 is stored, plotted, and/or otherwise modeled. Laboratory data is typically more accurate than on-line sensor data shown at 102 because of the sophistication of the equipment used in the laboratory environment employed to evaluate machine oil. But, the laboratory data is typically not as recent as the on-line sensor data which the information management system requests from interface 22, FIGS. 3-4.

In this example, the machine was sampled three times in the past three months and the laboratory reported a total asset number (TAN) value of approximately 0.5 each time. See plot 100. The stored TAN limit 104 for this particular machine is 1.5. The sensor data 102 (e.g., produced by a dielectric sensor) provides a measurement of oil quality. As shown, the trend for the laboratory TAN data 100 conflicts with the sensor data 102 (possibly due, for example, to a sensor reset at time stamp 106).

The information management system is programmed to periodically apply a model to the sensor data and the laboratory data especially when there is a noted discrepancy between the two as shown after time stamp 106. In one example, the model is:

$$\text{TAN(realtime)} = \text{Tan(last laboratory measurement} + \beta \text{ (sensor data)} + \gamma \tag{1}$$

where $\beta$ is a constant set at the factory and $\gamma$ is set at $\frac{1}{16}$.

Thus, the modeled TAN curve shown at 110, especially after time stamp 108, is a function of the laboratory data and the sensor data.

At time stamp 108, for example, equation (1) is calculated to produce estimate plot 110 for the TAN fluid parameter and, at time stamp 112 (between the time when the previous lab data was available and the next lab data will be available at time stamp 114), the TAN value is expected to reach and exceed the alarm limit 104. In response, the information management system outputs the recommendation: "TAN will exceed limit on Feb. 15, 2016. Change the oil and perform an engine overhaul."

Figure 7:
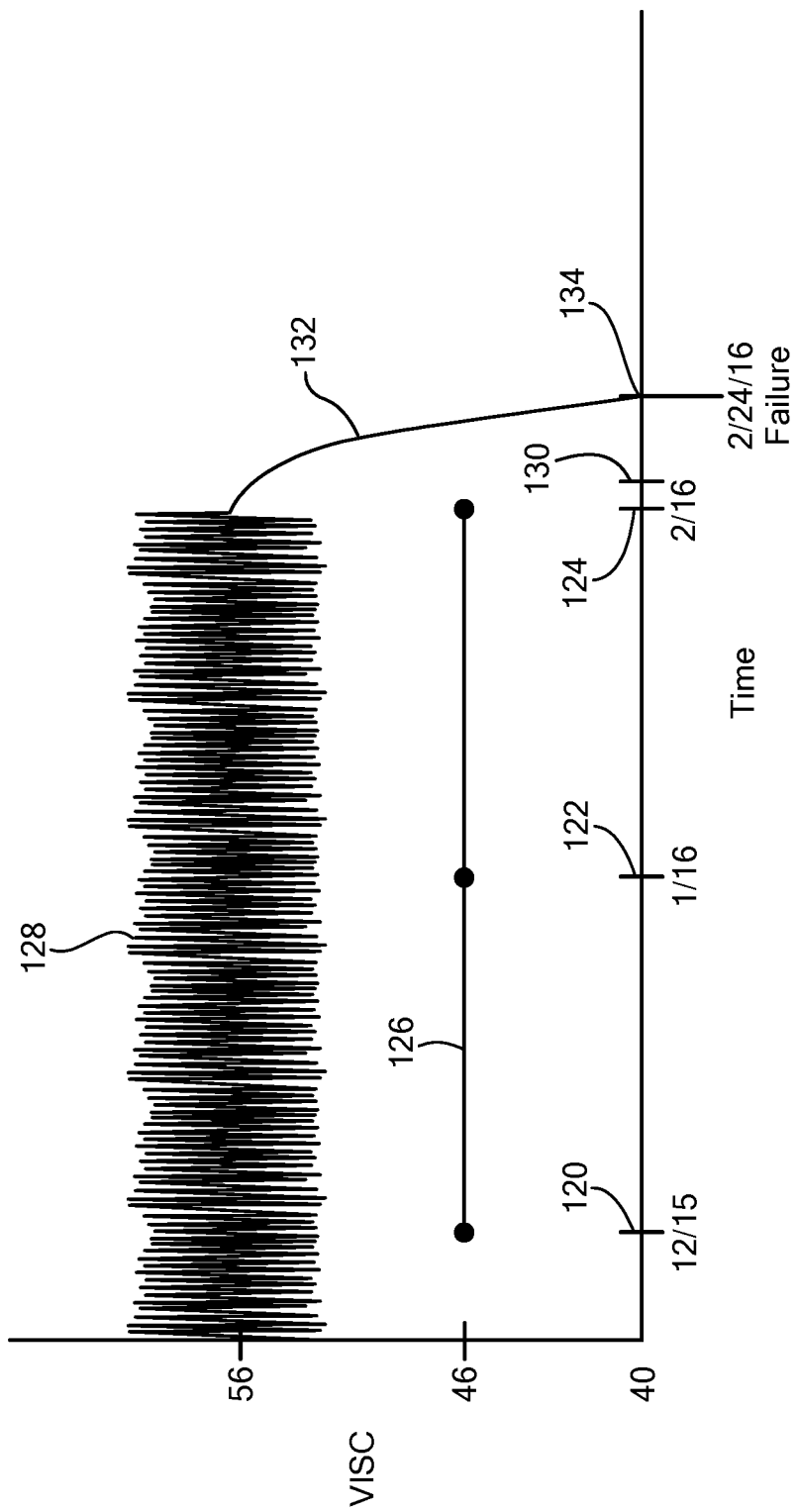
FIG. 7 is an exemplary graph showing plotted laboratory data, plotted sensor data, and a model used to normalize the sensor data to the laboratory data in order to determine when a machine oil parameter will reach a set alarm limit.

In another example shown in FIG. 7, lab viscosity measurements for oil in a machine at time stamps 120, 122, and 124 are uploaded or otherwise stored and plotted as shown at 126. The sensor (viscometer) data is shown at 128 per request from the information management system to the interface. There is a discrepancy between the lab data and the sensor data.

A model is used thus:

$$\min \lfloor ((\text{Lab}-\alpha\text{sensor}))_{12/15}^2 + ((\text{lab}-\alpha\text{sensor}))_{1/16}^2 + ((\text{lab}-\alpha\text{sensor}))_{2/16}^2 \rfloor \quad (2)$$

in order to solve for $\alpha$. Now, the normalized output of the sensor data is:

$$\text{visc,sensor normalized} = \alpha \text{visc,sensor,raw} \quad (3)$$

The normalized calculation can be projected out in time based on a $4^{th}$ order polynomial fit updating in real time with new data every five minutes with equal weight. This function to normalize the sensor viscosity data to the probably more reliable laboratory data can be run at time stamp 130 to reveal an estimated trend plotted at 132 revealing a normalized viscosity level of 40 (the alarm limit) at future time stamp 134. As a result, the information management system outputs the following recommendation: change oil and inspect engine on Feb. 24, 2016.

In the past, highly skilled and experienced scientists (typically with advanced degrees) would normally attempt to manually reconcile laboratory data and sensor data for various fluid parameters.

In this new system, much of that reconciliation is automated. The models discussed above and others are programmed, stored in, and executed automatically by the information management system. Still, sensor data (uploaded, for example, every five minutes) and laboratory data (uploaded, for example, every month) can be displayed to any user as shown in FIG. 8 at 140 and 142, respectively, by the information management system.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A fluid sensor/plant machinery monitoring system interface complex comprising:
   a plurality of on-line fluid property sensors outputting on-line sensor data and connected to an interface configured with a server outputting the on-line sensor data via a network;
   a remote information management system configured to:
      request and receive said on-line sensor data including fluid quality and viscosity via the network,
      store machine fluid property laboratory data including total asset number and viscosity data,
      calculate an estimate of one or more fluid properties including total asset number and viscosity based on both said received on-line sensor data and said stored laboratory data; and
   a fluid manifold unit receiving fluid from a machine and including ports for said on-line fluid property sensors.

2. The system of claim 1 in which the network is the internet.

3. The system of claim 1 in which the remote information management system calculates one or more fluid properties based on both said received on-line sensor data and said stored laboratory data based on models where a machine fluid property is a function of both the on-line sensor data and the stored laboratory data for the machine.

4. The system of claim 1 in which the interface include an instrument server and an information server.

5. The system of claim 4 in which the instrument server includes one or more sensor drivers configured to store the on-line sensor data in a memory.

6. The system of claim 5 in which the information server includes one or more web servers configured to retrieve the on-line sensor data from the memory and serving the on-line sensor data via the network to the remote information management system.

7. A fluid sensor/plant machinery monitoring system comprising:
   an interface connected to one or more on-line fluid property sensors outputting on-line sensor data and including:
      an instrument server configured to store the on-line sensor data in a memory, and
      an information server including at least one web server configured to retrieve the on-line sensor data from the memory and to serve the on-line sensor data to a network;
   a remote information management system configured to:
      request and receive the on-line sensor data including fluid quality and viscosity via the network,
      store machine fluid property laboratory data including total asset number and viscosity data,
      calculate one or more machine fluid properties including total asset number and viscosity based on models in which a machine fluid property is a function of the on-line sensor data and the stored fluid property laboratory data; and
   a fluid manifold unit receiving fluid from a machine and including ports for said on-line fluid property sensors.

8. The system of claim 7 in which the network is the internet.

9. A fluid monitoring method comprising:
   coupling a fluid manifold with at least one on-line fluid property sensor to receive fluid from a machine to provide sensor data;
   providing said sensor data to a common interface;

serving the sensor data from the common interface to a remote information management system via a network;

providing machine fluid property laboratory data including total asset number and viscosity data to the information management system; and executing one or more models stored in the information management system to calculate an estimate of one or more machine fluid properties including total asset number and viscosity as a function of both the machine fluid property laboratory data and the sensor data.

10. A fluid sensor/plant machinery monitoring method comprising:

connecting a fluid manifold unit to a machine to receive fluid from the machine;

coupling one or more on-line fluid property sensors to the manifold unit;

connecting an interface to the one or more on-line fluid property sensors outputting on-line sensor data;

storing the on-line sensor data in a memory;

serving the on-line sensor system data including fluid quality and viscosity to a remote management system via a network;

storing machine fluid property laboratory data including total asset number and viscosity data;

calculating one or more machine fluid properties including total asset number and viscosity based on one or more models in which a machine fluid property is a function of the on-line sensor data and the stored fluid property laboratory data.

\* \* \* \* \*